(12) United States Patent
Chen (10) Patent No.: US 8,721,535 B2
(45) Date of Patent: May 13, 2014

(54) TRACHEAL INTUBATION DEVICE

(76) Inventor: Tien-Sheng Chen, Taipei (TW)

( * ) Notice: Subject to any disclaimer, the term of this patent is extended or adjusted under 35 U.S.C. 154(b) by 83 days.

(21) Appl. No.: 13/354,388

(22) Filed: Jan. 20, 2012

(65) Prior Publication Data

US 2013/0066151 A1  Mar. 14, 2013

(30) Foreign Application Priority Data

Sep. 9, 2011 (TW) .............. 100132692 A (51) Int. Cl.
*A61B 1/267* (2006.01)
(52) U.S. Cl.
USPC .......................................... 600/188; 600/194
(58) Field of Classification Search
USPC ................................................. 606/188, 194
See application file for complete search history.

(56) References Cited

U.S. PATENT DOCUMENTS 4,306,547 A  12/1981 Lowell

2007/0106121 A1   5/2007 Yokota et al.
2008/0312507 A1 * 12/2008 Kim .............................. 600/188
2010/0312059 A1 * 12/2010 Mcgrath ....................... 600/188

OTHER PUBLICATIONS

Niforopoulou, P., Pantazopoulos, I., Demestiha, T., Koudouna, E. and Xanthos, T., Video-laryngoscopes in the adult airway management: a topical review of the literature, Acta Anaesthesiologica Scandinavica, Oct. 2010, pp. 1050-1061, vol. 54, Issue 9, © 2010 The Authors. Journal compilation © 2010 The Acta Anaesthesiologica Scandinavica Foundation, first published online.

* cited by examiner

*Primary Examiner* — Andrew Yang
(74) *Attorney, Agent, or Firm* — Alan Kamrath; Kamrath IP Lawfirm, P.A.

(57) ABSTRACT

A tracheal intubation device for placing an endotracheal tube in the trachea of a patient includes a bar-shaped camera, a handle portion, a guiding portion, and a display device. The bar-shaped camera for capturing images is placed inside the endotracheal tube. The display device is electrically connected to the bar-shaped camera for displaying images captured by the bar-shaped camera. The guiding portion connected to the handle portion has a front end and a rear end. The rear end is connected to the handle portion, and the bar-shaped camera and the endotracheal tube are movably situated in the guiding portion.

8 Claims, 7 Drawing Sheets

TRACHEAL INTUBATION DEVICE

BACKGROUND OF THE INVENTION

1. Field of the Invention

The present invention relates to a medical device. More specifically, the present invention relates to a tracheal intubation device for placing an endotracheal tube into the trachea of a patient.

2. Description of the Related Art

For apnea patients, tracheal intubation is an essential operation for sustaining respiration to maintain the vital signs of a patient. Medical personnel have to place an endotracheal tube into the trachea of a patient to ensure that oxygen is provided in a short period of time. Therefore, it is an important task for medical personnel to place the endotracheal tube efficiently. In practice, tracheal intubation devices equipped with a camera are often used by medical personnel to confirm the location of the trachea of a patient and then to place the endotracheal tube into the trachea of the patient. Tracheal intubation devices disclosed in U.S. Pat. No. 4,306,547 and US Patent Publication Number 2007/0106121 are the most widely used tracheal intubation devices, and the image capturing device of each tracheal intubation device is installed on the lateral side of the endotracheal tube slot. When the glottis of the trachea of the patient is observed via the image capturing device, medical personnel push the endotracheal tube installed on the lateral side of the image capturing device into the trachea of the patient.

Although the tracheal intubation device disclosed in Patent Number 2007/0106121 does improve the process of tracheal intubation, some drawbacks during operation of the device need to be eliminated. Sometimes, due to the physical structure of a patient, the visual field of this kind of tracheal intubation device is blocked by the parallax caused by the camera installed on the lateral side of the endotracheal tube slot, or the endotracheal tube. Consequently, since the glottis of the trachea cannot be observed, the endotracheal tube cannot be precisely placed into the trachea of a patient by medical personnel. The Acta Anaethesiologica Scandinavica published in 2010 (2010; 54(9):1050-61) also indicates that this widely used tracheal intubation devices may occasionally fail in precise placement.

In view of the fact that efficient intubation is critical for the survival of a patient, there is a need to provide an intubation device by which intubation can be performed easily and precisely.

SUMMARY OF THE INVENTION

It is an object of the present invention to provide a tracheal intubation device by which an intubation procedure can be operated easily and precisely.

To achieve the abovementioned object, the tracheal intubation device of the present invention comprises a bar-shaped camera, a handle portion, a guiding portion, and a display device. The bar-shaped camera is placed inside the endotracheal tube for capturing images. The display device is electrically connected to the bar-shaped camera for displaying images captured by the bar-shaped camera. The guiding portion is connected to the handle portion. The guiding portion comprises a front end and a rear end, and the rear end of the guiding portion is connected to the handle portion. The bar-shaped camera and the endotracheal tube are movably situated in the guiding portion.

According to one embodiment of the present invention, the tracheal intubation device of the present invention further comprises an insertion unit mounted on the bar-shaped camera for placing inside the endotracheal tube to allow the bar-shaped camera to move in synchrony with the endotracheal tube.

According to another embodiment of the present invention, the bar-shaped camera is made of a rigid material that allows the bar-shaped camera to guide the direction of movement of the endotracheal tube while the endotracheal tube is moving.

DETAILED DESCRIPTION OF THE PREFERRED EMBODIMENTS

The advantages and innovative features of the invention will become more apparent from the following detailed descriptions when taken together with the accompanying drawings.

Figure 1:
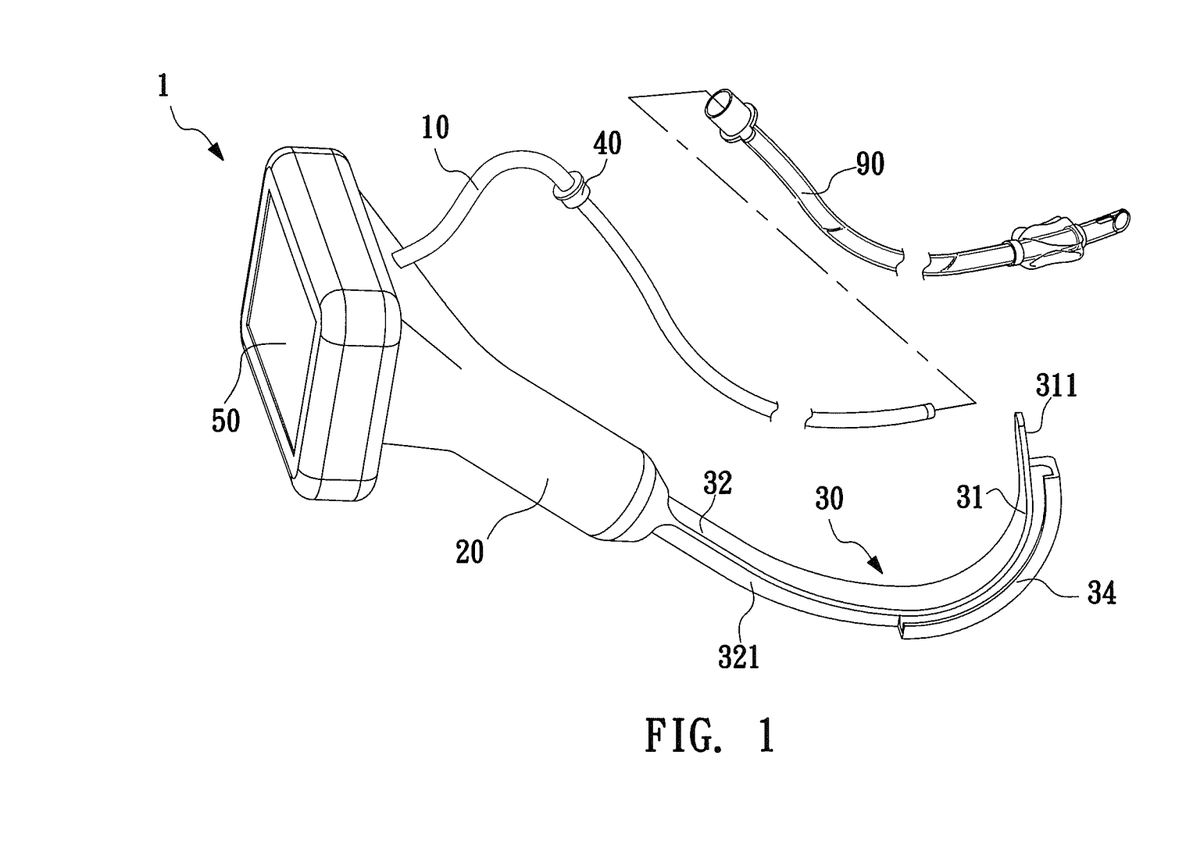
FIG. 1 is an exploded view illustrating one embodiment of the tracheal intubation device of the present invention and the endotracheal tube.
Figure 2:
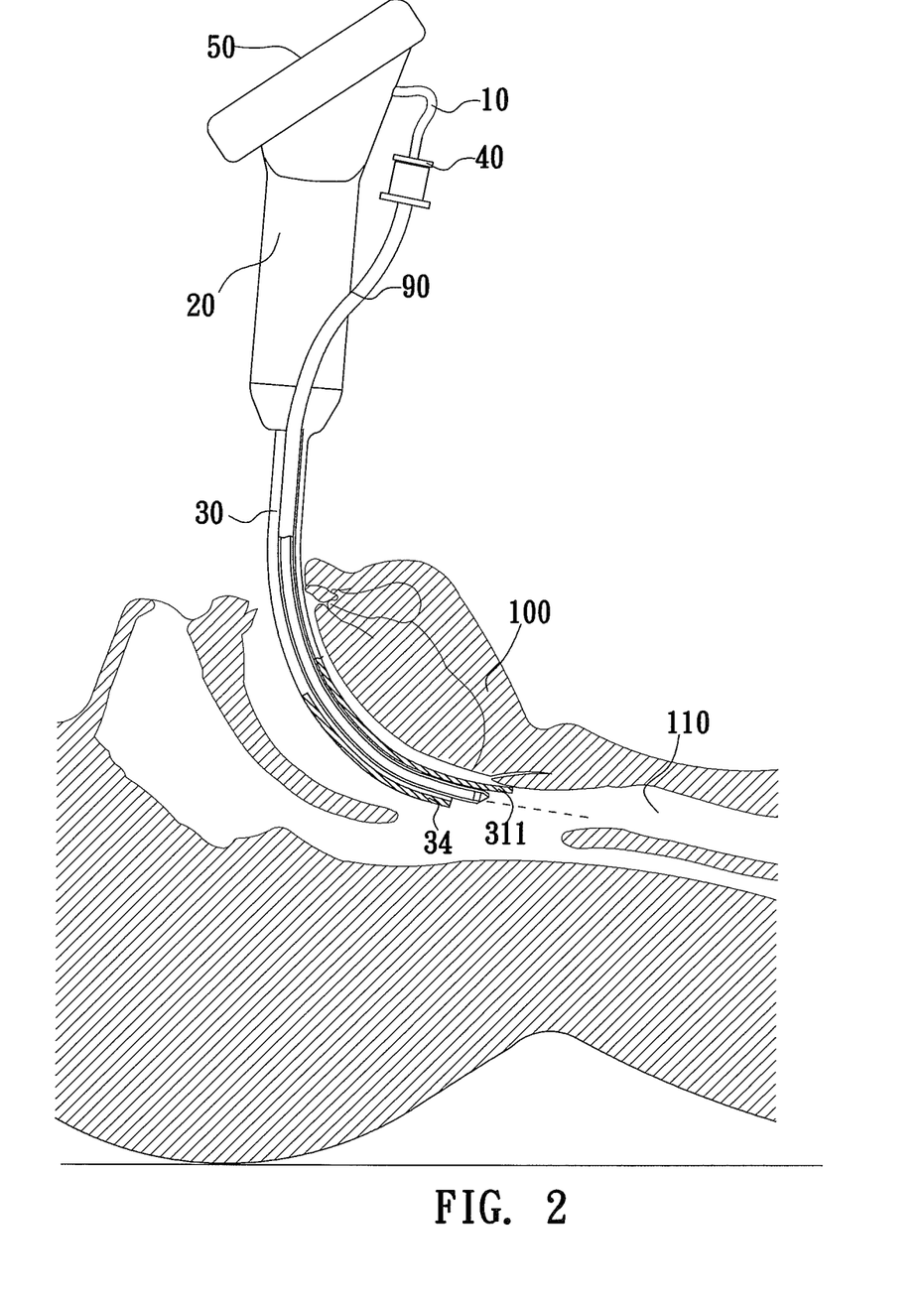
FIG. 2 is a schematic drawing illustrating a usage state of one embodiment of the tracheal intubation device of the present invention.
Figure 3:
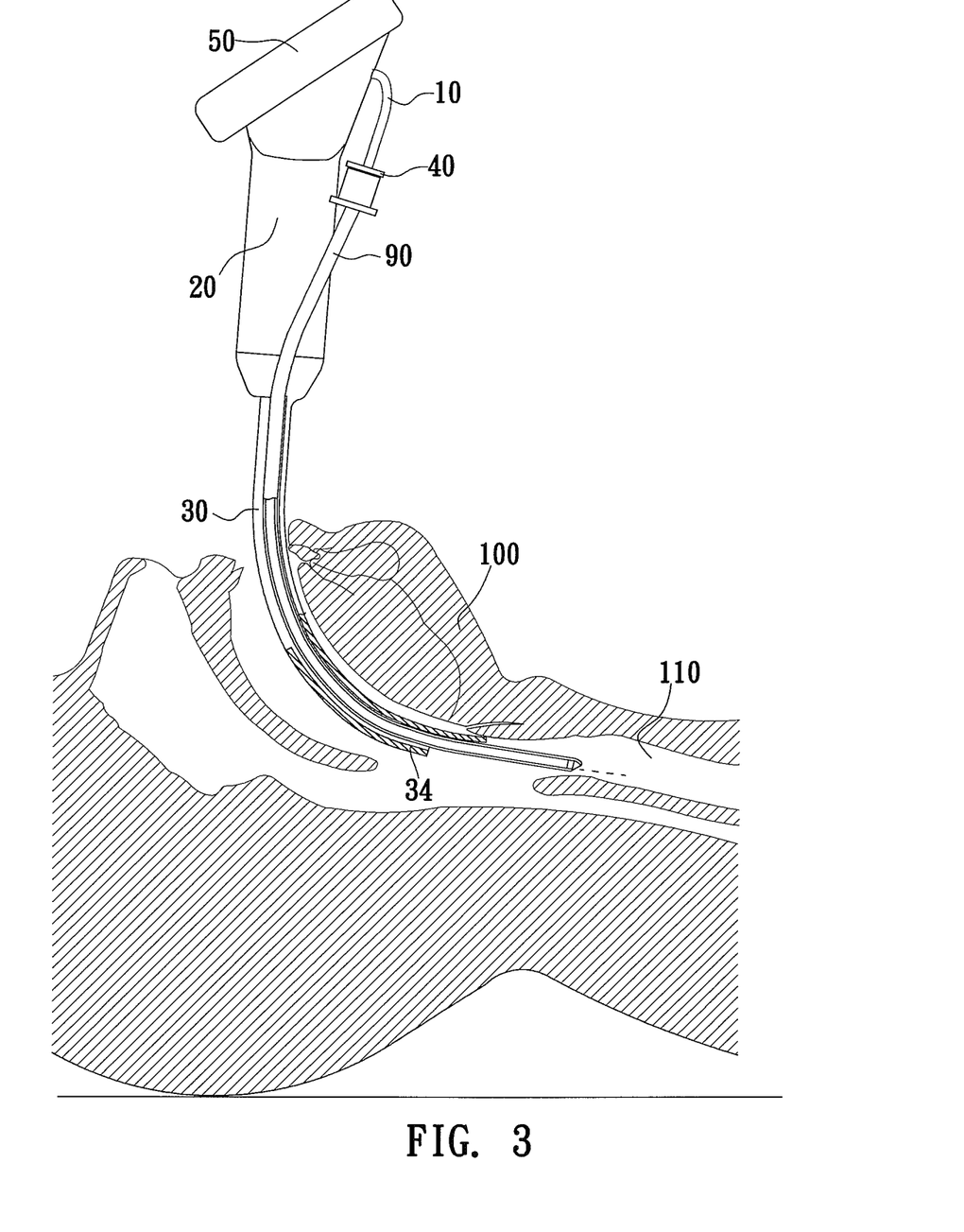
FIG. 3 is another schematic drawing illustrating the usage state of one embodiment of the tracheal intubation device of the present invention.
Figure 4:
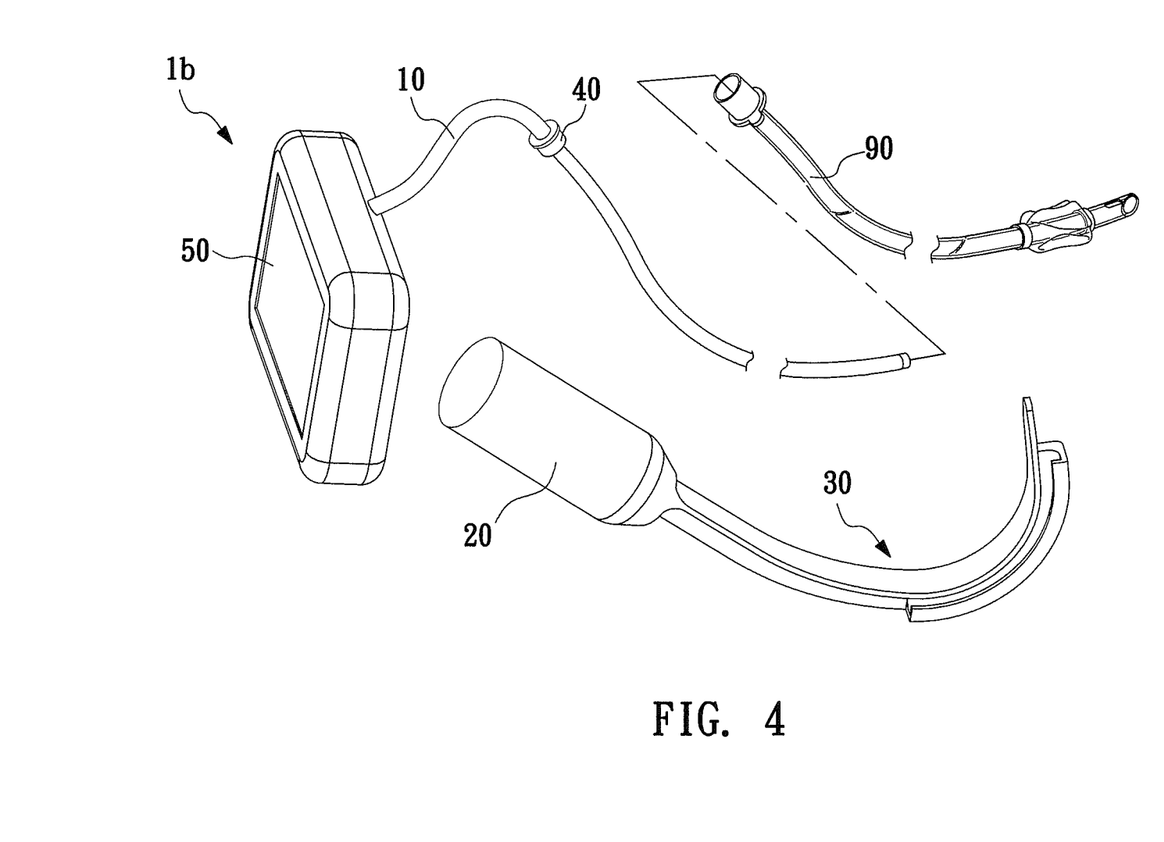
FIG. 4 is an exploded view illustrating another embodiment of the tracheal intubation device of the present invention and the endotracheal tube.

Please refer to FIG. 1 to FIG. 4, depicting embodiments of the tracheal intubation device of the present invention, FIG. 1 is an exploded view illustrating one embodiment of the tracheal intubation device of the present invention and the endotracheal tube. FIG. 2 is a schematic drawing illustrating a usage state of one embodiment of the tracheal intubation device of the present invention. FIG. 3 is another schematic drawing illustrating the usage state of one embodiment of the tracheal intubation device of the present invention. FIG. 4 is an exploded view illustrating another embodiment of the tracheal intubation device of the present invention and the endotracheal tube.

According to one embodiment of the present invention, as shown in FIG. 1, the tracheal intubation device 1 of the present invention comprises a bar-shaped camera 10, a handle portion 20, a guiding portion 30, an insertion unit 40, and a display device 50. The bar-shaped camera 10 is placed inside the endotracheal tube 90 to ensure that the endotracheal tube 90 can be precisely placed into the glottis of the trachea by reference to the image captured by the bar-shaped camera 10. The bar-shaped camera 10 is used for capturing images, such as an image of the glottis of the trachea of a patient. The display device 50 is electrically connected to the bar-shaped camera 10 for displaying the image captured by the bar-shaped camera 10. As shown in FIG. 1, the guiding portion 30 is connected to the handle portion 20, and the guiding portion 30 comprises a front end 31, a rear end 32, and a slot 34. The rear end 32 of the guiding portion 30 is connected to the handle portion 20, and the slot 34 is situated at the front end 31 of the guiding portion 30. The bar-shaped camera 10 and the endotracheal tube 90 are movably situated in the slot 34 of the guiding portion 30. It is noted that the front end 31 of the guiding portion 30 in this embodiment further comprises a protrusion part 311, and that the slot 34 does not extend to the protrusion part 311. The rear end 32 of the guiding portion 30 forms a passage 321 to facilitate the placement of the endotracheal tube 90 and the bar-shaped camera 10 for entering the slot 34, as shown in FIG. 2 and FIG. 3. The insertion unit 40 is mounted on the bar-shaped camera 10 for placing inside the endotracheal tube 90 to allow the bar-shaped camera 10 to move in synchrony with the endotracheal tube 90, shown in FIG. 3, to ensure that the position of the bar-shaped camera 10 relative to the endotracheal tube 90 remains unchanged during movement; i.e., the bar-shaped camera 10 always stays inside the endotracheal tube 90 while the endotracheal tube 90 is moving.

It is noted that the bar-shaped camera 10 is a soft tube in this embodiment. The front end of the bar-shaped camera 10 has a camera and an illuminating device such as an LED light bulb. The display device 50 is connected to the handle portion 20, but the present invention is not limited to this embodiment. As shown in FIG. 4, the display device 50 of the tracheal intubation device 1b can be connected only to the bar-shaped camera 10 and detached from the handle portion 20. The shape of the guiding portion 30 is an arch curving from the rear end 32 to the front end 31, and the curve matches the curve of a human's oral cavity. The inner parts of the guiding portion 30 of this embodiment are an integrated form. The insertion unit 40 of this embodiment is a plastic plug, but the present invention is not limited to the abovementioned embodiment. The insertion unit 40 can be made of another material, and any device capable of placing the bar-shaped camera 10 inside the endotracheal tube 90 is applicable.

As shown in FIG. 2, when the tracheal intubation device 1 of the present invention is used, the guiding portion 30 is used for lifting the tongue base of the patient 100, and the bar-shaped camera 10 and the endotracheal tube 90 in the slot 34 all enter the mouth of the patient 100. The protrusion part 311 of the guiding portion 30 also has guiding and orienting functions for allowing the bar-shaped camera 10 and the endotracheal tube 90 to move toward the glottis of the trachea precisely. Medical personnel only have to push the bar-shaped camera 10 and the endotracheal tube 90 into the throat of the patient 100 until the medical personnel observes the accurate location of the trachea 110 of the patient 100 via the display device 50. Then, the endotracheal tube 90 is pushed to detach the endotracheal tube 90 from the insertion unit 40. At which point, the endotracheal tube 90 is placed in the trachea 110.

It is noted that the tracheal intubation device 1 of the present invention not only can prevent the visual field of the glottis of the trachea from being misled due to the camera's parallax or being blocked by the inserted endotracheal tube but also can prevent damage to the upper respiratory tissue during intubation. Furthermore, because the bar-shaped camera 10 of the tracheal intubation device 1 of the present invention is placed inside the endotracheal tube 90, the volume of the guiding portion 30 of the tracheal intubation device 1 of the present invention can be reduced. Consequently, the guiding portion 30 can be placed into a mouth of the patient 100 easily, even in the case of patients with smaller mouths, shorter necks, or thicker tongues. Moreover, placing the bar-shaped camera 10 inside the endotracheal tube 90 allows the bar-shaped camera 10 to enter the trachea 110 together with the endotracheal tube 90 to ensure that the endotracheal tube 90 is placed into the trachea 110 precisely each time, without risk of failure.

Figure 5:
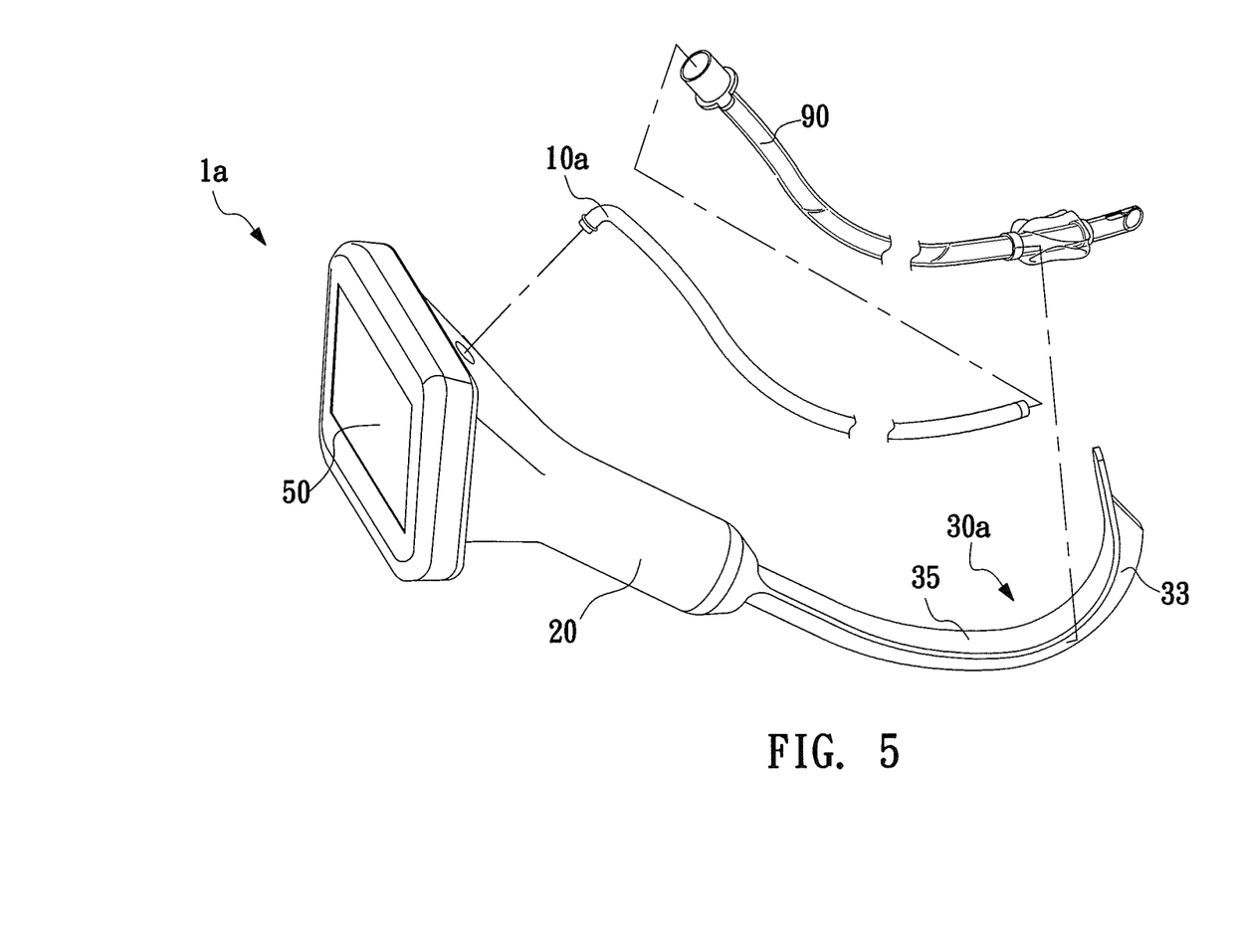
FIG. 5 is an exploded view illustrating a further embodiment of the tracheal intubation device of the present invention and the endotracheal tube.

FIG. 5 is an exploded view illustrating another embodiment of the tracheal intubation device of the present invention and the endotracheal tube.

The difference between the tracheal intubation device 1a of this embodiment and the tracheal intubation device 1 is that the guiding portion 30a of the tracheal intubation device 1a comprises a tongue piece 35 and a barrier 33. The tongue piece 35 is substantially perpendicular to the barrier 33. The bar-shaped camera 10a of the tracheal intubation device 1a in this embodiment is detachably connected to the handle portion 20, and the bar-shaped camera 10a is made of a rigid material that is curved to guide the direction of movement of the endotracheal tube 90 while it is moving. The bar-shaped camera 10 and the endotracheal tube 90 in this embodiment are accommodated within an area formed by the tongue piece 35 and the barrier 33, and the endotracheal tube 90 and the bar-shaped camera 10 can be moved within the area formed by the tongue piece 35 and the barrier 33. The usage and operating procedure of the tracheal intubation device 1a are the same as those of the tracheal intubation device 1. Therefore, the description is omitted. For such information, please refer to FIG. 2 and FIG. 3.

Figure 6:
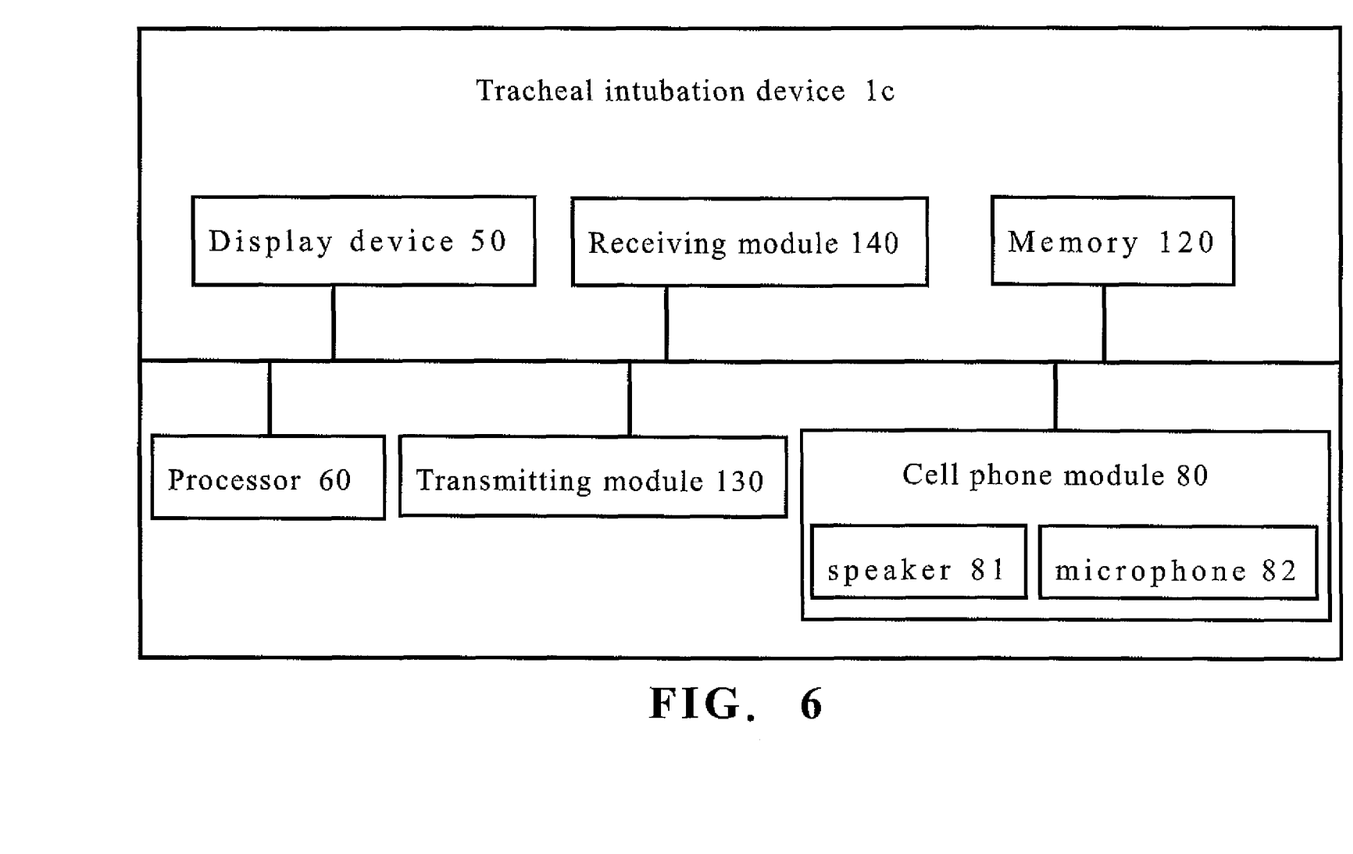
FIG. 6 is a structural drawing of a further embodiment of the tracheal intubation device of the present invention.
Figure 7:
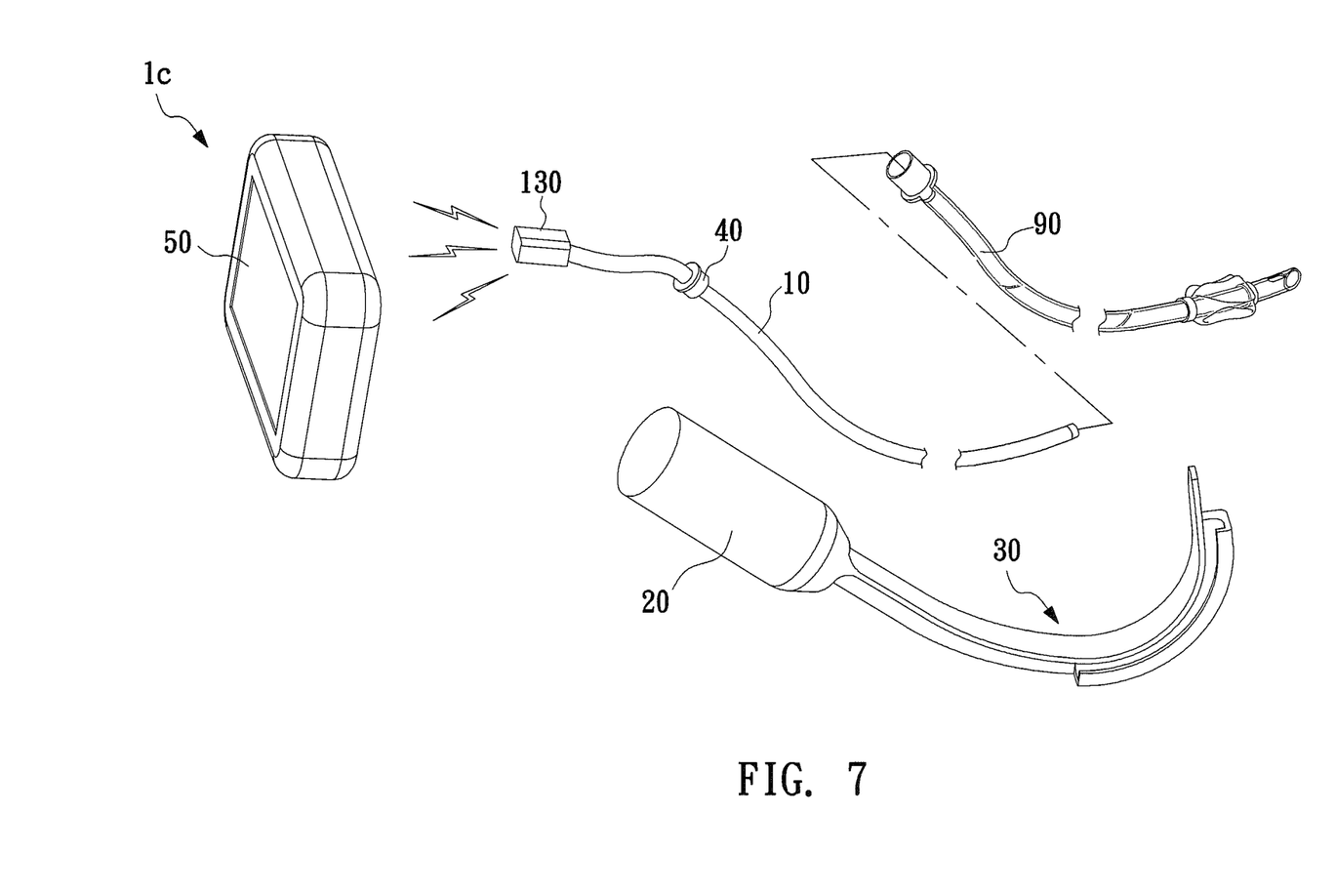
FIG. 7 is another exploded view illustrating a further embodiment of the tracheal intubation device of the present invention.

Please refer to FIG. 6 and FIG. 7, related to another embodiment of the tracheal intubation device of the present invention. FIG. 6 is a structural drawing of another embodiment of the tracheal intubation device of the present invention. FIG. 7 is another exploded view illustrating another embodiment of the tracheal intubation device of the present invention.

As shown in FIG. 6, the tracheal intubation device 1c of the present invention further comprises a processor 60, a receiving module 140, a cell phone module 80, a memory 120, and a transmitting module 130. The processor 60, the receiving module 140, the cell phone module 80, and the memory 120 are separately electrically connected to the display device 50. For example, electronic components like the processor 60 can be placed inside the shell of the display device 50, and the transmitting module 130 is connected to the bar-shaped camera 10. In this embodiment, the display device 50 is an individual display monitor. Images captured by the bar-shaped camera 10 are transmitted to the receiving module 140 via the transmitting module 130 and displayed on the display device 50 afterwards. Moreover, the cell phone module 80 comprises a speaker 81 and a microphone 82 for allowing medical personnel to talk to rescue personnel via the cell phone module 80. The memory 120 is used for storing images captured by the bar-shaped camera 10 and other essential control programs. The processor 60 is used for implementing the operations mentioned above. It is noted that the receiving module 140 and the transmitting module 130 both can be wireless communication devices employing a method such as Bluetooth, and the memory 120 can be a memory card. It is noted that the abovementioned devices and modules can also be installed in the tracheal intubation device 1, 1a, or 1b of the present invention. However, the present invention is not limited to this embodiment.

It must be noted that the above-mentioned embodiments are only for illustration. It is intended that the present invention covers modifications and variations of this invention provided that they fall within the scope of the following claims and their equivalents. Therefore, it will be apparent to those skilled in the art that various modifications can be made to the structure of the present invention without departing from the scope or spirit of the invention.

What is claimed is:

1. A tracheal intubation device for placing in a trachea of a patient, wherein the tracheal intubation device comprises:
   an endotracheal tube;
   a bar-shaped camera placed inside the endotracheal tube for capturing an image;
   a handle portion;
   a display device electrically connected to the bar-shaped camera for displaying the image captured by the bar-shaped camera;
   a guiding portion connected to the handle portion comprising a front end, a rear end, and a slot for accommodating the endotracheal tube and the bar-shaped camera, wherein the rear end of the guiding portion is connected to the handle portion, wherein the bar-shaped camera and the endotracheal tube are movably situated in the guiding portion, wherein the slot is mounted at the front end of the guiding portion and a passage is formed at the rear end of the guiding portion to facilitate placement of the endotracheal tube and the bar-shaped camera into the slot, wherein the front end further comprises a protrusion part, wherein the slot does not extend to the protrusion part;
   an insertion unit mounted on the bar-shaped camera for placing inside the endotracheal tube;
   a processor;
   a receiving module;
   a cell phone module;
   a memory; and
   a transmitting module, wherein the processor, the receiving module, the cell phone module, and the memory are separately electrically connected to the display device and the transmitting module is connected to the bar-shaped camera.

2. The tracheal intubation device as claimed in claim 1, wherein the display device and the handle portion are connected.

3. The tracheal intubation device as claimed in claim 1, wherein the guiding portion comprises a tongue piece and a barrier; and wherein the tongue piece is substantially perpendicular to the barrier.

4. The tracheal intubation device as claimed in claim 3, wherein the endotracheal tube and the bar-shaped camera are accommodated within an area formed by the tongue piece and the barrier.

5. The tracheal intubation device as claimed in claim 4, wherein the bar-shaped camera is made of a rigid material that allows the bar-shaped camera to guide a direction of movement of the endotracheal tube while the endotracheal tube is moving.

6. The tracheal intubation device as claimed in claim 5, wherein the bar-shaped camera is detachably connected to the handle portion.

7. A tracheal intubation device for placing in a trachea of a patient, wherein the tracheal intubation device comprises:
   an endotracheal tube;
   a bar-shaped camera placed inside the endotracheal tube for capturing an image;
   a handle portion;
   a display device electrically connected to the bar-shaped camera for displaying the image captured by the bar-shaped camera;
   a guiding portion connected to the handle portion comprising a front end and a rear end, wherein the rear end of the guiding portion is connected to the handle portion, wherein the bar-shaped camera and the endotracheal tube are movably situated in the guiding portion, wherein the guiding portion comprises a tongue piece and a barrier, wherein the tongue piece is substantially perpendicular to the barrier, wherein the endotracheal tube and the bar-shaped camera are accommodated within an area formed by the tongue piece and the barrier, wherein the bar-shaped camera is made of a rigid material that allows the bar-shaped camera to guide a direction of movement of the endotracheal tube while the endotracheal tube is moving, wherein the bar-shaped camera is detachably connected to the handle portion;
   a processor;
   a receiving module;
   a cell phone module;
   a memory; and
   a transmitting module, wherein the processor, the receiving module, the cell phone module, and the memory are separately electrically connected to the display device and the transmitting module is connected to the bar-shaped camera.

8. The tracheal intubation device as claimed in claim 7, wherein the display device and the handle portion are connected.

* * * * *